Feb. 12, 1974 F. W. ANDERSON Plant Pat. 3,479
PLUM TREE
Filed Oct. 13, 1972
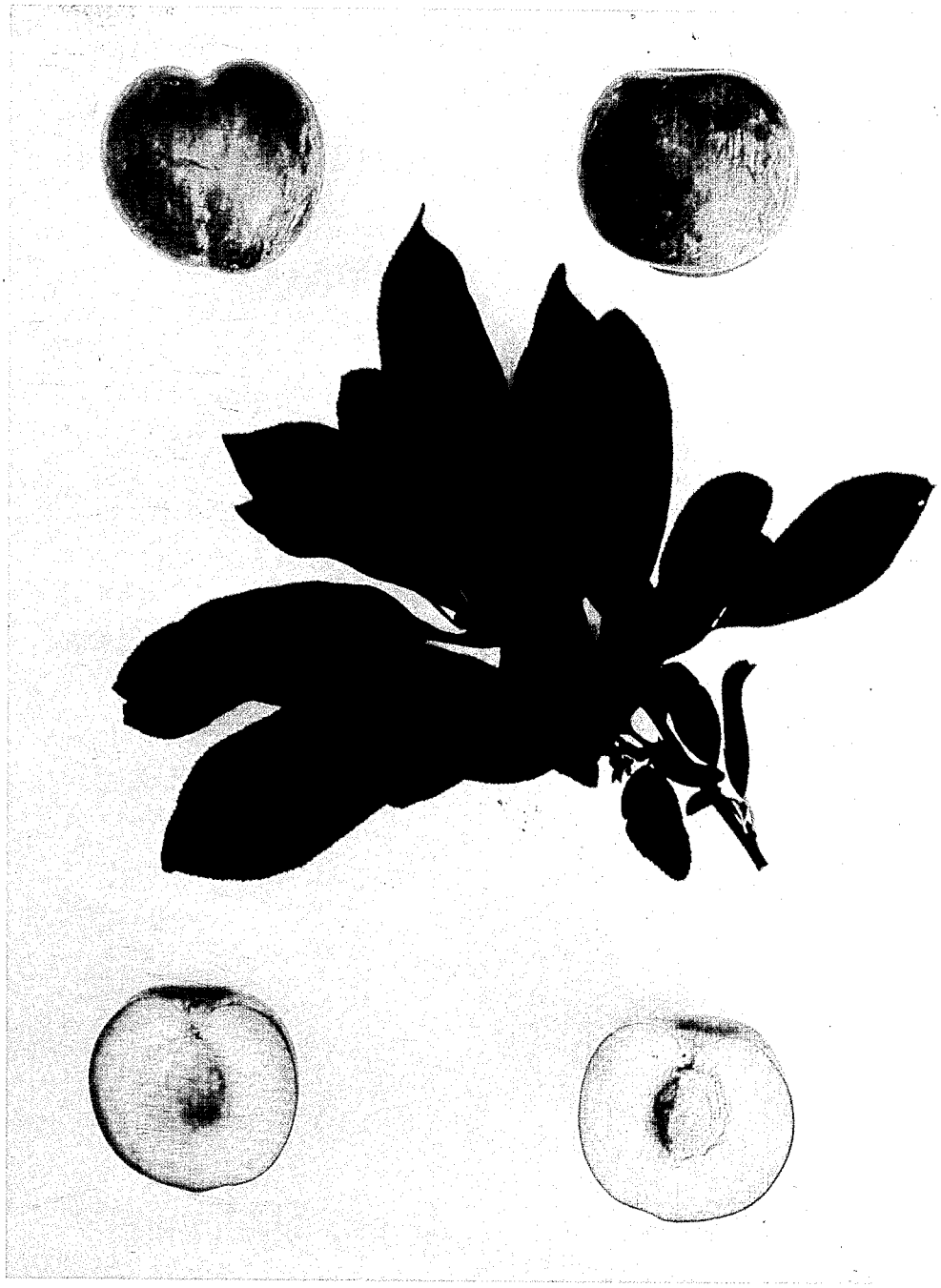

United States Patent Office

Plant Pat. 3,479
Patented Feb. 12, 1974

3,479

PLUM TREE

Frederic W. Anderson, Merced, Calif., assignor to Reedley Nursery, Inc., Reedley, Calif.

Filed Oct. 13, 1972, Ser. No. 297,869
Int. Cl. A01h 5/03
U.S. Cl. Plt.—38 1 Claim

ABSTRACT OF THE DISCLOSURE

A plum tree which is of medium size, vigorous, spreading, open, round-topped, foliated with large obovate leaves, and a regular and very productive bearer of large, freestone, uniform, symmetrical, globose fruit having deep purple-red skin with a silver-blue bloom, buff-yellow flesh, and a light tan stone.

Background of the variety: Over a substantial number of years I have engaged in an extensive and continuing plant breeding program at my experimental nursery and orchard located near Le Grand, Merced County, California; one purpose of such program being to provide improved varieties of fruit trees. The present variety of plum tree resulted from my endeavors in the conduct of such plant breeding program.

Origin of the variety: The present variety of plum tree was originated by me in my experimental nursery and orchard, located as aforesaid, as an open-pollinated seedling of the Eldorado plum (unpatented). Seeds, which I gatherer from an Eldorado plum tree were planted in such nursery, and the resultant seedlings were maintained by me under careful and continuing observation. When such seedlings bore fruit, one evidenced commercially desirable characteristics, and I, therefore, selected such one seedling (which is the present variety) for asexual reproduction and preparatory to introduction of the variety to the trade.

Asexual reproduction of the variety: Subsequent to origination and selection by me of the present variety of plum tree in the manner above described, I asexually reproduced it by top-working on mature trees in my said orchard, and—in maturity—such reproductions ran true to the original tree in all respects.

Summary of the variety: The present variety of plum tree is of medium size, vigorous, spreading, open, round-topped, foliated with large obovate leaves, and a regular and very productive bearer of large, freestone, uniform, symmetrical, globose fruit having deep purple-red skin with a silver-blue bloom, buff-yellow flesh, and a light tan stone.

The present variety of plum tree is additionally characterized by fruit which somewhat resembles the fruit of the Eldorado and likewise has an unusually long shelf life, and hence is well adapted for storage and long distance shipping. Further, in particular comparison, the fruit of the present variety is larger, bears more heavily, and ripens approximately two weeks later, thus desirably extending the market period of this type of fruit.

Brief description of the drawing: The drawing is an illustration, by photographic reproduction in color, of leaves and detached fruit of the present variety of plum tree; one fruit being cut in half to expose the flesh, and the stone remaining in place in one such cut half.

Description of the variety: The botanical details of this new and distinct variety of plum tree—with color definitions (except those in common color terms) referenced to Maerz and Paul Dictionary of Color—are as follows:

Tree:
- *Size.*—Medium.
- *Vigor.*—Vigorous.
- *Growth.*—Spreading.

- *Density.*—Open.
- *Form.*—Round-topped.
- *Productivity.*—Very productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Brown.

Leaves:
- *Size.*—Large, Average length—4". Average width—1⅝".
- *Form.*—Obovate, Acuminate, Abruptly pointed.
- *Thickness.*—Thin.
- *Texture.*—Smooth.
- *Margin.*—Crenate.
- *Petiole.*—Medium length, Medium thickness.
- *Glands.*—Average number—2. Opposite to alternate, Medium size, Reniform, Red. Positioned on base of blade.
- *Color.*—Top side—Medium green (23–L–9). Under side—Lighter green (22–H–6).

Flower buds:
- *Size.*—Medium.
- *Length.*—Medium.

Flowers:
- *Blooming period.*—Date of first bloom: Feb. 26, 1972. Date of full bloom: Mar. 10, 1972. Medium, as compared with other varieties.

Fruit:
- *Maturity when described.*—Eating ripe—Aug. 12, 1972.
- *Date of first picking.*—Aug. 1, 1972.
- *Date of last picking.*—Aug. 15, 1972.
- *Size.*—Uniform, Large. Average diameter axially—2¼". Average transversely in suture plane—2¼".
- *Form.*—Uniform, symmetrical, globose.
- *Suture.*—Shallow. Extends from base to beyond, but discontinuous at apex. Slight depression beyond pistil point.
- *Ventral surface.*—Rounded slightly.
- *Lips.*—Equal.
- *Cavity.*—Rounded. Elongated in suture plane with suture showing on both sides. Average depth—⅝". Average breadth—9/16".
- *Base.*—Truncate.
- *Apex.*—Short, rounded, depressed.

Skin:
- *Thickness.*—Medium.
- *Texture.*—Tough.
- *Tenacity.*—Tenacious to flesh.
- *Tendency to crack.*—None noted.
- *Down.*—Wanting.
- *Color.*—Deep purple-red (48–L–3) with sliver-blue bloom.

Flesh:
- *Juice.*—Moderate.
- *Texture.*—Very firm. Meaty to melting.
- *Fibers.*—Few, fine.
- *Ripens.*—Evenly.
- *Flavor.*—Mild.
- *Aroma.*—Wanting.
- *Eating quality.*—Fair to good.
- *Color.*—Buff-yellow (11–K–6).

Stone:
- *Type.*—Free. Retains short fiber-like threads along ridges.
- *Size.*—Meduim. Average length—⅞". Average breadth—11/16. Average thickness—7/16".
- *Form.*—Oblong.

*Base.*—Oblique.
*Hilum.*—Oblong.
*Apex.*—Acute.
*Sides.*—Equal.
*Ventral edge.*—Thick, without wing.
*Dorsal edge.*—Narrow, with narrow groove toward base.
*Tendency to split.*—Slight.
*Color.*—Light tan (13–J–8).

Use. Market—long distance shipping.
Keeping quality: Excellent—unusually long shelf life.
Resistance to insects and diseases: No unusual susceptibilities noted.
Shipping quality: Excellent.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, which is of medium size, vigorous, spreading, open, round-topped, foliated with large, obovate leaves, and a regular and very productive bearer of large, freestone, uniform, symmetrical, globose fruit having deep purple-red skin with a silver-blue bloom, buff-yellow flesh, and a light tan stone, the variety being further characterized by fruit which somewhat resembles the fruit of the Eldorado and likewise has an unusually long shelf life, but—in particular comparison—is larger, bears more heavily, and ripens approximately two weeks later.

No references cited.

ROBERT E. BAGWILL, Primary Examiner